United States Patent [19]

Kirkpatrick et al.

[11] 4,272,279
[45] Jun. 9, 1981

[54] SEMICARBAZIDYL PHTHALIDES AND USE AS PLANT GROWTH REGULATORS

[75] Inventors: Joel L. Kirkpatrick, Washington Crossing, Pa.; Natu R. Patel, Overland Park, Kans.

[73] Assignee: Gulf Oil Corporation, Pittsburgh, Pa.

[21] Appl. No.: 161,189

[22] Filed: Jun. 19, 1980

[51] Int. Cl.³ .................... A01N 43/08; C07D 307/88
[52] U.S. Cl. ........................... 71/88; 260/343.3 R
[58] Field of Search .................. 260/343.3 R; 71/88

[56] References Cited

U.S. PATENT DOCUMENTS

| | | | |
|---|---|---|---|
| 3,985,773 | 10/1976 | Alt et al. | 260/343.3 R |
| 3,990,880 | 11/1976 | Mumford | 260/343.3 R |
| 4,094,661 | 6/1978 | Alt et al. | 71/88 |
| 4,148,625 | 4/1979 | Nagase | 260/343.3 R |

*Primary Examiner*—Henry R. Jiles
*Assistant Examiner*—Jane T. Fan
*Attorney, Agent, or Firm*—Carl A. Cline

[57] ABSTRACT

New compounds of the general structural formula

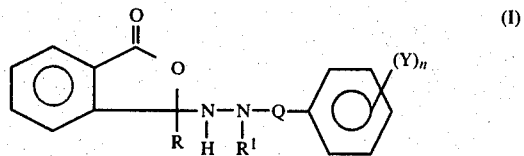

are disclosed, in which Q is one of the following:

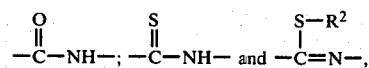

R is methyl or ethyl, R¹ is H or lower alkyl, R² is lower alkyl and Y represents substituents, alike or unlike, selected from the following group: lower alkyl, lower alkoxy, lower alkylthio, bromo, chloro, fluoro, cyano, trifluoromethyl and 1-methylene and n=0 to 3, which are useful as plant growth regulators, both in the basic form illustrated above and also as the hydrohalide salts.

54 Claims, No Drawings

SEMICARBAZIDYL PHTHALIDES AND USE AS PLANT GROWTH REGULATORS

DESCRIPTION OF THE INVENTION

The present invention is directed to a novel class of semicarbazidyl phthalides of the general structural formula

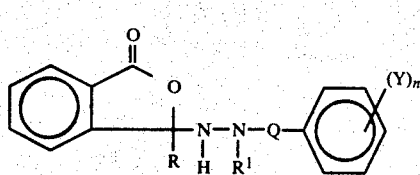

in which Q represents one of the following structures;

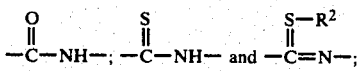

R is methyl or ethyl, $R^1$ is H or lower alkyl, $R^2$ is lower alkyl and Y represents substituents, alike or unlike, selected from the group consisting of lower alkyl, lower alkoxy, lower alkylthio, bromo, chloro, fluoro, cyano, trifluoromethyl and 1-methylene and n=0 to 3, and hydrohalide salts thereof. The term "lower" above refers to $C_1$ to $C_4$ substituent groups.

The present invention is also directed to methods of regulating the growth of plants and agricultural formulations therefor, comprising the novel compounds as active plant growth regulators.

SYNTHESIS OF THE COMPOUNDS

The compounds may be prepared by means of the reaction scheme illustrated below:

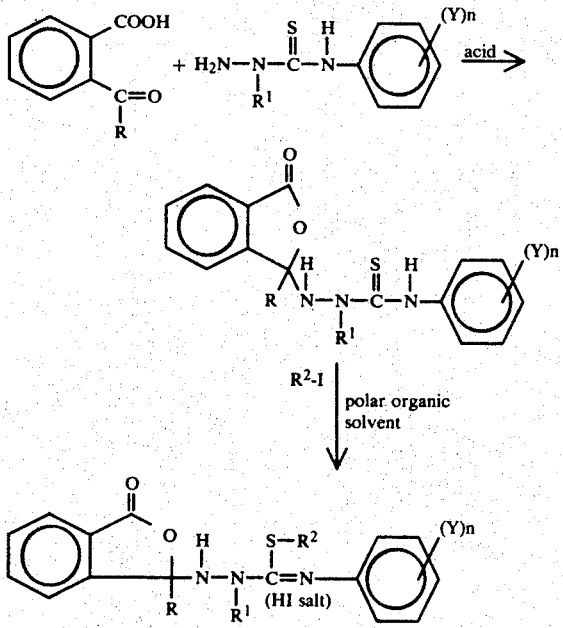

The hydrazinethiocarboxanilide intermediate of the above scheme may be conveniently made by known methods by reacting an alkylhydrazine, for example, with a phenyl isothiocyanate.

The condensation of the o-acylbenzoic acid with the hydrazinethiocarboxanilide is an acid-catalyzed condensation which may be carried out at ambient, or room temperature. Various acids may be used to promote the condensation and better contact between the reactants may be obtained by use of a non-reactive organic solvent. Glacial acetic acid is a convenient condensation catalyst because it also possesses useful solvent ability and is easily removed from the product by washing.

For the conversion of compounds in which Q is

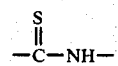

to those in which Q is

a strong alkylating reagent such as methyl iodide is preferred, employing a non-reactive polar organic solvent as reaction medium. Typical solvents are dimethylformamide, acetone and ether.

A solvent should be chosen in which the reactants have substantial solubility, in order to obtain the reaction product quickly and efficiently. These products are obtained in the form of hydriodide salts and may be used in this form, as conversion to the free base is unnecessary for the purpose of use to regulate growth of plants.

The following synthesis procedures are presented by way of illustration.

Preparation of 3-Methyl-3-[2'-methyl-4'-(4-fluorophenyl)-3-thiosemicarbazidyl]phthalide To a suspension of 2.0 g (0.01 mole) of 2-methyl-4-(4'-fluorophenyl)-3-thiosemicarbazide is 30 ml of glacial acetic acid was added 1.7 g (0.01 mole) of 2-acetylbenzoic acid. After stirring at room temperature for 16 hours, water was added and the resulting solid collected by filtration, washed with water and dried giving 1.1 g, mp: 136°–138°.

Preparation of 1-(3-Methyl-3-phthalidyl)-2,3-dimethyl-4-phenylisothiosemicarbazide Hydroiodide (1) To 5 ml of dry dimethylformamide, 3.2 g. of 3-methyl-3-(2-methyl-4-phenyl-3-thiosemicarbazidyl)-phthalide and 5 ml. of methyl iodide were added. The mixture was stirred at room temperature, then 150 ml. of dry ether was added, the mixture was stirred and the clear liquid was decanted. The oily residue was stirred with about 100 ml of ethyl acetate to give a whitish, finely divided solid which is recovered by filtration, was washed with ether and dried. The yield was 3.0 g., M.P. 145°–149° C.

(2) The above reaction was repeated with the use of acetone as a solvent. After the reactants were put in 25 ml. of dry acetone as reaction solvent and stirring was begun, a white precipitate appeared within one hour. Stirring was continued at room temperature overnight. The precipitate was recovered by filtration, was washed with acetone, then with dry ether and was dried. The yield was 3.2 g. of white powder, m.p. 156°–159° C. This product was of better purity than the product of the first procedure, but the purity of both products was adequate for use in regulation of growth of plants.

In the following table there are listed compounds which have been prepared by means of the reactions outlined and illustrated above.

TABLE 1

COMPOUNDS OF THE FORMULA

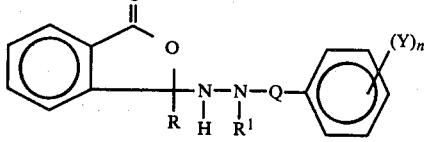
(I)

| Compound Number | R | R¹ | Q | R² | (Y)$_n$ | | M.P. °C. |
|---|---|---|---|---|---|---|---|
| 4061 | CH$_3$ | CH$_3$ | —CSNH— | — | 4-fluoro | | 136–138 |
| 4336 | CH$_3$ | " | " | — | 3-methyl | | 69–71 |
| 4337 | " | " | " | — | 4-Br | | 129–130 |
| 4338 | " | " | " | — | n = 0 | | 132–136 |
| 4345 | " | CH$_3$ | —CSNH— | — | 2-fluoro | | 145–148 |
| 4346 | " | " | " | — | 4-methyl | | 145–148 |
| 4347 | " | " | " | — | 3-CF$_3$ | | 153–154 |
| 4348 | " | " | " | — | 3,4-dichloro | | 125–126 |
| 4349 | " | " | " | — | 2,4-dimethyl | | 160–162 |
| 4350 | " | " | —CONH— | — | n = 0 | | 178–180 |
| 4351 | " | " | —CSNH— | — | 4-iodo | | 123–125 |
| 4352 | " | " | " | — | 4-cyano | | 158–159 |
| 4353 | " | " | " | — | 2,5-dimethyl | | 122–123 |
| 4354 | " | " | " | — | 3-chloro | | 94–95 |
| 4533 | " | H | —CONH— | — | n = 0 | | 183–185 |
| 4598 | " | CH$_3$ | " | — | 2-methyl | | glass-like |
| 4599 | " | " | —CONH— | — | 3-chloro | | 144–148 |
| 4600 | " | " | " | — | 4-fluoro | | 175–177 |
| 4601 | " | " | " | — | 3-bromo | | 152–155 |
| 4613 | " | " | " | — | 3-Cl—4-CH$_3$ | | 180–182 |
| 4614 | " | " | " | — | 2,3-dimethyl | | 143–146 |
| 4615 | " | " | " | — | 3-methyl | | 122–127 |
| 4616 | " | " | " | — | 4-chloro | | 189–190 |
| 4617 | " | " | " | — | 2-chloro | | 158–159 |
| 4618 | " | " | " | — | 4-isopropyl | | 123–128 |
| 4619 | " | " | " | — | 4-methoxy | | 169–172 |
| 4620 | " | " | " | — | 3-chloro-4-fluoro | | 164–166 |
| 4698 | " | " | " | — | 2-CF$_3$ | | 139–142 |
| 4699 | CH$_3$ | CH$_3$ | —CONH— | — | 2,4-difluoro | | 203–204 |
| 4700 | " | " | " | — | 4-bromo | | 163–166 |
| 4701 | " | " | " | — | 2-CF$_3$—4-Cl | | 159–161 |
| 4776 | " | " | " | — | 2-fluoro | | 186–188 |
| 4777 | " | " | " | — | 3-fluoro | | 155–158 |
| 4778 | " | " | " | — | 4-ethyl | | 170–172 |
| 4779 | " | " | " | — | 4-nitro | | 216–217 |
| 4780 | " | " | —CSNH— | — | 3,5-dichloro | | 162–164 |
| 4781 | " | " | " | — | 4-butyl | | 133–136 |
| 4782 | " | " | " | — | 3-bromo | | 108–112 |
| 4783 | " | " | " | — | 2-methoxy | | 164–166 |
| 4784 | " | " | " | — | 3-chloro-4-methyl | | 140–143 |
| 4818 | " | " | " | — | 2-CF$_3$ | | 143–145 |
| 4819 | " | " | " | — | 4-CF$_3$ | | 177–180 |
| 4820 | " | " | " | — | 2,6-dichloro | | 167–170 |
| 4821 | " | " | " | — | 2,6-dimethyl | | 190–192 |
| 4822 | " | " | " | — | 2-bromo | | 148–151 |
| 4823 | " | " | " | — | 3-CF$_3$—4-Cl | | 147–149 |
| 4824 | " | " | " | — | 4-methoxy | | 148–150 |
| 4825 | " | " | " | — | 3,4-dimethyl | | 150–151 |
| 4826 | " | " | " | — | 1-methylene | | 116–119 |

(benzyl instead of —⟨phenyl⟩—(Y)$_n$)

| | | | | | | | |
|---|---|---|---|---|---|---|---|
| 4755 | " | " | S—R²<br>\|<br>—C=N— | CH$_3$ | n = 0 | (HI salt) | 156–159 |
| 4833 | " | " | " | CH$_3$ | 3-fluoro | (HI salt) | 155–158 |
| 4834 | " | " | " | " | 4-ethyl | (HI salt) | 139–141 |
| 4835 | " | " | " | —C$_2$H$_5$ | n=0 | (HI salt) | 156–158 |
| 4837 | " | " | " | CH$_3$ | 4-isopropyl | (HI salt) | 139–141 |
| 4838 | " | " | " | " | 4-chloro | (HI salt) | 145–147 |
| 4839 | " | " | " | " | 4-ethoxy | (HI salt) | 117–119 |
| 4840 | " | " | " | " | 2-methyl-4-chloro | (HI salt) | 124–126 |
| 4934 | " | " | " | " | 3-methoxy | (HI salt) | 143–146 |
| 4928 | " | " | " | " | 2-methyl | (HI salt) | 125–129 |
| 4930 | " | " | " | " | 2,4-dimethyl | (HI salt) | 127–129 |
| 4933 | " | " | " | " | 3-chloro-4- | (HI salt) | 149–151 |

TABLE 1-continued

COMPOUNDS OF THE FORMULA

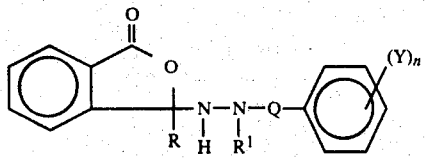

(I)

| Compound Number | R | R¹ | Q | R² | (Y)$_n$ | M.P. °C. |
|---|---|---|---|---|---|---|
| 4941 | " | " | " | " | methyl 3,4-dichloro (HI salt) | 121–123 |
| 4943 | ethyl | CH$_3$ | —CONH— | — | 4-methyl | 163–165 |
| 4857 | CH$_3$ | H | —CSNH— | — | 3-chloro-4-methyl | 144–152(dec.) |
| 4858 | " | " | " | — | 2,4-dimethyl | 132–134 |
| 4859 | " | " | " | — | 4-isopropyl | 130–139 |
| 4860 | " | CH$_3$ | " | — | 2-cyano | 139–141 |
| 4861 | " | " | " | — | 4-ethoxy | 142–143 |
| 4862 | " | " | " | — | 2-methyl | 152–154 |
| 4863 | " | " | " | — | 3-methoxy | 124–126(dec.) |
| 4864 | " | " | " | — | 2-methyl-4-chloro | 135–137 |
| 4865 | " | " | " | — | 4-chloro | 165–166(dec.) |
| 4866 | " | " | " | — | 4-isopropyl | 148–150(dec.) |
| 4869 | " | " | —CONH— | — | 4-SCH$_3$ | 185–186 |
| 4870 | " | " | " | — | 3-SCH$_3$ | 128–130 |
| 4871 | " | " | " | — | 2-methyl-6-isopropyl | 108–110 |
| 4872 | " | " | " | — | 3-methoxy | 96–98 |
| 4873 | " | " | " | — | 2-methoxy | 170–172 |
| 4874 | " | " | " | — | 4-methyl | 172–173 |
| 4875 | " | " | " | — | 2-ethoxy | 165–167 |
| 4876 | " | " | " | — | 2,6-dimethyl | 163–165 |
| 4877 | " | " | " | — | 2,6-dichloro | 166–168 |
| 4878 | " | " | " | — | 3-CF$_3$—4-Cl | 159–161 |
| 4879 | " | " | " | — | 2-methyl-5-chloro | 158–160 |
| 4880 | " | " | " | — | 2-methyl-3-chloro | 174–175 |
| 4881 | " | " | " | — | 3-chloro-4,6-dimethoxy | 204–206 |
| 4882 | " | " | " | — | 2-chloro-6-methyl | 174–176 |
| 4883 | " | " | " | — | 4-butyl | 170–172 |
| 4884 | " | " | " | — | 4-butoxy | 164–166 |
| 4885 | " | " | " | — | 2,6-dimethyl-4-bromo | 153–155 |

USE OF THE GROWTH REGULATORS

In highly active compounds, growth regulating effects, often of phytotoxic severity resulting from pre-emergent and post-emergent application are readily apparent. These effects may be demonstrated by means of the following illustrative procedures.

PRE-EMERGENT APPLICATION

Disposable paper trays about 2½ inches deep were filled with soil and sprayed with aqueous spray mixtures at a rate of 5 lb. of active chemical per acre of sprayed area, were seeded with 6 species of plant seeds and were then covered with about ¼ inch of soil. The spray mixtures were prepared by dissolving the proper amount of growth regulator compound in 15 ml of acetone, adding 4 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 60 ml by addition of warm water. Twenty-one days after seeding and treatment the plantings were examined and plant injury was rated according to the following schedule:

| DEGREE OF EFFECT | | |
|---|---|---|
| 0 | = | no effect |
| 1 | = | slight effect, plants recovered |
| 2 | = | moderate effect, injury to 26 to 75 percent |
| 3 | = | severe effect, injury to 76 to 99 percent |
| 4 | = | of foilage maximum effect (all plants died) |

POST-EMERGENT APPLICATION

Several species of plants were grown in potting soil in disposable expanded cellular polystyrene trays and tomatoes were grown in four-inch pots in the greenhouse. Aqueous spray formulations were prepared and the growing plants were sprayed at a spray volume of 60 gallons per acre and an application rate of 5 lb. per acre. Spray mixtures were prepared in the manner described above. For comparative purposes, plants were also sprayed at 60 gal./acre with a spray mixture containing no growth regulator. Plant injury was again rated according to the schedule disclosed above and observations of growth regulator effects were observed and recorded as follows:

| Effect | Abbreviation in Tables |
|---|---|
| Formative effect on new growth | F |
| Epinasty | E |
| Growth reduction | G |
| Non-emergence | K |
| Necrosis | N |

The following plant species were employed in the tests made according to the foregoing procedures:

| Number | Species |
|---|---|
| I | *Digitaria sanguinalis* |
| II | *Celosia plumosa* |
| III | *Bromus inermis* |
| IV | *Setaria italica* |
| V | *Raphanus sativus* |
| VI | *Beta vulgaris* |
| VII | *Medicago sativa* |
| VIII | *Avena sativa* |
| IX | *Lycopersicum esculentum* |

In Table 2 below there are tabulated various observations of pre- and post-emergent herbicidal and growth regulator effects of the growth regulator compounds of this invention.

acre. One large, more mature tomato plant was included in the test along with the other, smaller growing plants. For comparative purposes, plants were also sprayed at a spray volume of 40 gallons per acre with a spray mixture containing no growth regulator.

Approximately fifteen days after spraying, the plants were observed and the results were evaluated according to the schedule disclosed above. Results obtained with representative compounds are presented in Table 3. The test species are as follows:

| Number | Common Name | Scientific Name |
|---|---|---|
| I | Pigweed | *Amaranthus retroflexus* |
| II | Lambsquarters | *Chenopodium album* |

TABLE 2
EFFECTS OF COMPOUNDS ON PLANT LIFE

| Compound Number | Pre-emergent Effects | | | | | | Post-emergent Effects | | | | | |
|---|---|---|---|---|---|---|---|---|---|---|---|---|
| | I | II | III | IV | V | VI | IV | VII | VIII | V | VI | IX |
| 4061 | F2G2 | F2G2 | F3G2 | F1 | F3G3 | F3G3 | 0 | F3G3 | 0 | F2N2 | F3G3 | F2G2 |
| 4336 | F1G1 | F3G2 | F3G3 | F3G2 | F3G2 | F3G2 | F1G1 | F3G3 | F1 | N1 | N4 | F2 |
| 4337 | 0 | 0 | 0 | 0 | 0 | F1 | N4 | N4 | 0 | N1G1 | N4 | N2 |
| 4338 | F1G1 | F3G3 | F3G2 | F2G1 | F3G2 | F3G2 | N3G3 | F3G3 | 0 | N3G3 | N4 | F3 |
| 4345 | 0 | N3G3 | N1G1 | 0 | N1G1 | G2N1 | N3G2 | N3G2 | N1 | N1G1 | N3G3 | N2 |
| 4346 | 0 | N2 | 0 | 0 | 0 | 0 | N3G2 | N2G1 | 0 | 0 | N2AG2 | N1 |
| 4347 | 0 | F3G2 | F1 | F1 | F1 | F2G1 | G2F1 | F3G2 | F1G1 | F2G1 | F3G2 | F3G1 |
| 4348 | 0 | N2G2 | 0 | 0 | 0 | 0 | N4 | F3G3 | N1 | N4 | N4 | N2G2 |
| 4349 | 0 | 0 | F1 | 0 | 0 | 0 | N1 | F1 | 0 | 0 | F1 | 0 |
| 4350 | F2G2 | F3G2 | F3G3 | F3G2 | F3G3 | F3G3 | F2G2 | F3G2 | F1 | F1G1 | F3G2 | F3 |
| 4351 | 0 | 0 | 0 | 0 | 0 | 0 | N4 | F2G2 | F1 | N2G1 | N4 | N1 |
| 4352 | 0 | 0 | F1 | 0 | 0 | F2 | N4 | N4 | N1 | N2 | N4 | N2G1 |
| 4353 | 0 | 0 | 0 | 0 | 0 | 0 | N1G1 | N2G1 | 0 | N1 | N3G3 | N1 |
| 4354 | F2G2 | K4 | F3G3 | F3G2 | F2G2 | F2G2 | N3G2 | F3G3 | F1 | N2G2 F1 | N4 | F2N1 |
| 4533 | F2G1 | F2G1 | F3G2 | F2G1 | F2G2 | F2G2 | F2G2 | F3G3 | F1G1 | F1G1 | F3G2 | F3G2 |

POST-EMERGENT APPLICATION AT LOWER RATES ON 24 SPECIES

Twenty-four species of plants were grown in potting soil in disposable styrofoam trays and tomatoes were grown in four-inch pots in the greenhouse. Aqueous spray formulations were prepared and the growing plants were sprayed at a spray volume of 40 gallons per acre and application rates of 3 lb. and 1 lb. per acre. The spray mixtures were prepared by dissolving the proper amount of growth regulator compound in 15 ml of acetone, adding 4 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 80 ml by addition of warm water. Of this spray mixture, a 50 ml portion was used to spray the plants at a rate of 3 lb. per acre of sprayed area. The remaining 30 ml. was diluted to 90 ml. with warm water and was used to spray the plants at a rate of 1 lb. per

| Number | Common Name | Scientific Name |
|---|---|---|
| III | Crabgrass | *Digitaria sanguinalis* |
| IV | Downey brome | *Bromus tectorum* |
| V | Giant foxtail | *Setaria faberii* |
| VI | Nutsedge | *Cyperus esculentus* |
| VII | Peanuts | *Arachis hypogaea* |
| VIII | Cotton | *Gossypium herbaceum* |
| IX | Tomato | *Lycopersicum esculentum* |
| X | Sugar beets | *Beta vulgaris* |
| XI | Wild buckwheat | *Polygonum convolvulus* |
| XII | Wild mustard | *Brassica kaber* |
| XIII | Mature tomato plant | *Lycopersicum esculentum* |
| XIV | Cocklebur | *Xanthium pensylvanicum* |
| XV | Morning glory | *Ipomea purpurea* |
| XVI | Soybeans | *Soja max* |
| XVII | Barnyard grass | *Echinochloa crusgalli* |
| XVIII | Green foxtail | *Setaria viridis* |
| XIX | Alfalfa | *Medicago sativa* |
| XX | Corn | *Zea mays* |
| XXI | Grain sorghum | *Sorghum vulgare* |
| XXII | Shattercane | *Sorghum bicolor* |
| XXIII | Wheat | *Triticum aestivum* |
| XXIV | Wild oats | *Avena fatua* |
| XXV | Rice | *Oryza sativa* |

TABLE 3
POST-EMERGENT EFFECTS ON 24 SPECIES

| Species | Appl'n. Rate (lb/A) | Compound Nos. | | | | | | | | |
|---|---|---|---|---|---|---|---|---|---|---|
| | | 4336 | 4337 | 4338 | 4776 | 4777 | 4778 | 4779 | 4780 | 4781 |
| I | 3 | 3 | 2 | 3 | F1G1 | F3G3 | 0 | 0 | F3G3 | N2F1 |
| | 1 | — | 0 | 3 | 0 | F3G3 | 0 | 0 | F2G1 | 0 |
| II | 3 | 3 | 2 | 3 | F1 | F3G3 | F1 | 0 | F3G3 | N3F1 |
| | 1 | — | 1 | 2 | 0 | F3G3 | 0 | 0 | F2G1 | 0 |
| III | 3 | 1 | 0 | 0 | 0 | F2G2 | 0 | 0 | 0 | 0 |
| | 1 | — | 0 | 0 | 0 | F1G1 | 0 | 0 | 0 | 0 |
| IV | 3 | 0 | 0 | 0 | 0 | F1G1 | 0 | 0 | 0 | 0 |
| | 1 | — | 0 | 0 | 0 | 0 | 0 | 0 | 0 | 0 |

TABLE 3-continued
POST-EMERGENT EFFECTS ON 24 SPECIES

| | | | | | | | | | | |
|---|---|---|---|---|---|---|---|---|---|---|
| V | 3 | 1 | 0 | 0 | 0 | F3G2 | 0 | 0 | 0 | F1G1 |
| | 1 | — | 0 | 0 | 0 | F2G1 | 0 | 0 | 0 | 0 |
| VI | 3 | 0 | 0 | 1 | 0 | F1 | 0 | 0 | 0 | 0 |
| | 1 | — | 0 | 0 | 0 | 0 | 0 | 0 | 0 | 0 |
| VII | 3 | 0 | 0 | 0 | 0 | F1 | 0 | 0 | 0 | 0 |
| | 1 | — | 0 | 0 | 0 | F1 | 0 | 0 | 0 | 0 |
| VIII | 3 | 2 | 1 | 3 | N2F1 | F3G3 | N1F1 | 0 | N2F3 | N1F2 |
| | 1 | — | 0 | 2 def. | F1 | F3G3 | 0 | 0 | F2G2 | 0 |
| IX | 3 | 1 | 1 | 3 | F1 | F3G3 | F1 | 0 | F2 | F1 |
| | 1 | — | 0 | 2 | 0 | F2G1 | 0 | 0 | F1 | 0 |
| X | 3 | 3G | 3G | 3 | F1 | F3G3 | F1 | F1 | F2G2 | F1 |
| | 1 | — | 2G | 2 | F1 | F2G1 | 0 | 0 | F2 | F1 |
| XI | 3 | 1 | 2 | 2 | 0 | F3G3 | F1 | 0 | F2G2 | 0 |
| | 1 | — | 2 | 1 | 0 | F2G2 | 0 | 0 | F1 | 0 |
| XII | 3 | 1 | 1 | 2 | F2G2 | F3G3 | F1 | 0 | F2G2 | F1 |
| | 1 | — | 0 | 2 | F2G2 | F3G2 | 0 | 0 | F2 | 0 |
| XIII | 3 | | | | F2 | F3G2 | F1 | F1 | F3 | F1 |
| | 1 | | | | F1 | F3G1 | 0 | 0 | F2 | 0 |
| XIV | 3 | 0 | 1 | 1 | 0 | F2G2 | 0 | 0 | F2 | 0 |
| | 1 | — | 0 | 0 | 0 | F1 | 0 | 0 | 0 | 0 |
| XV | 3 | 1 | 1 | 1 | F1 | F3G3 | 0 | 0 | F2G2 | 0 |
| | 1 | — | 0 | 0 | 0 | F2G1 | 0 | 0 | 0 | 0 |
| XVI | 3 | 3G | 3G | 2 | N1F1 | F3G3 | F1 | F1 | F3G3 | F1 |
| | 1 | — | 1G | 2 | 0 | F3G3 | 0 | 0 | F2 | 0 |
| XVII | 3 | 1 | 0 | 1 | 0 | F2G2 | 0 | 0 | 0 | 0 |
| | 1 | — | 0 | 0 | 0 | F2G1 | 0 | 0 | 0 | 0 |
| XVIII | 3 | 1 | 0 | 1 | 0 | F3G2 | 0 | 0 | F1 | 0 |
| | 1 | — | 0 | 0 | 0 | F2G2 | 0 | 0 | 0 | 0 |
| XIX | 3 | 3 | 3 | 3 | F3 | F3G3 | F2 | 0 | F3G2 | F1 |
| | 1 | — | 2 | 2 | F2 | F3G1 | F1 | 0 | F2 | 0 |
| XX | 3 | 1 | 0 | 1 | 0 | F2G1 | 0 | 0 | 0 | 0 |
| | 1 | — | 0 | 0 | 0 | F1 | 0 | 0 | 0 | 0 |
| XXI | 3 | 2 | 0 | 3 | F2 | F3G2 | 0 | 0 | 0 | 0 |
| | 1 | — | 0 | 1 | F1 | F2G1 | 0 | 0 | 0 | 0 |
| XXII | 3 | 2 | 0 | 3 | F2 | F3G2 | 0 | 0 | 0 | 0 |
| | 1 | — | 0 | 1 | F1 | F2G1 | 0 | 0 | 0 | 0 |
| XXIII | 3 | 1 | 0 | 1 | 0 | F2G1 | 0 | 0 | 0 | 0 |
| | 1 | — | 0 | 0 | 0 | F1 | 0 | 0 | 0 | 0 |
| XXIV | 3 | 1 tillers | 0 | 1 | 0 | F1 | 0 | 0 | 0 | 0 |
| | 1 | — | 0 | 0 | 0 | 0 | 0 | 0 | 0 | 0 |
| XXV | 3 | 1 | 0 | 1 | 0 | F2 | 0 | 0 | 0 | 0 |
| | 1 | — | 0 | 0 | 0 | F1 | 0 | 0 | 0 | 0 |

| | Appl'n Rate | Compound Nos. | | | | | | | | |
|---|---|---|---|---|---|---|---|---|---|---|
| Species | (lb/A) | 4782 | 4783 | 4784 | 4818 | 4819 | 4820 | 4821 | 4822 | 4823 |
| I | 3 | F2G2 | F1 | F1G1 | F1 | 0 | N1 | 0 | 0 | 0 |
| | 1 | F2G1 | 0 | 0 | 0 | 0 | 0 | 0 | 0 | 0 |
| II | 3 | F2G2 | 0 | F1G1 | 0 | 0 | N1 | 0 | 0 | 0 |
| | 1 | F1G1 | 0 | 0 | 0 | 0 | 0 | 0 | 0 | 0 |
| III | 3 | 0 | 0 | 0 | 0 | 0 | 0 | 0 | 0 | 0 |
| | 1 | 0 | 0 | 0 | 0 | 0 | 0 | 0 | 0 | 0 |
| IV | 3 | 0 | 0 | 0 | 0 | 0 | 0 | 0 | 0 | 0 |
| | 1 | 0 | 0 | 0 | 0 | 0 | 0 | 0 | 0 | 0 |
| V | 3 | F1G1 | 0 | 0 | 0 | 0 | 0 | 0 | 0 | 0 |
| | 1 | 0 | 0 | 0 | 0 | 0 | 0 | 0 | 0 | 0 |
| VI | 3 | 0 | 0 | 0 | 0 | 0 | 0 | 0 | 0 | 0 |
| | 1 | 0 | 0 | 0 | 0 | 0 | 0 | 0 | 0 | 0 |
| VII | 3 | 0 | 0 | 0 | 0 | 0 | 0 | 0 | 0 | 0 |
| | 1 | 0 | 0 | 0 | 0 | 0 | 0 | 0 | 0 | 0 |
| VIII | 3 | N3F3 | N2F2 | N1F1 | N2 | F1 | N1 | 0 | N1 | 0 |
| | 1 | N3F3 | F1 | F1 | 0 | 0 | 0 | 0 | 0 | 0 |
| IX | 3 | F1 | F1 | 0 | F1 | 0 | N1 | 0 | F1 | 0 |
| | 1 | 0 | 0 | 0 | 0 | 0 | 0 | 0 | 0 | 0 |
| X | 3 | F2G1 | F1 | F1 | F1 | F1 | N1F1 | 0 | F1 | F1 |
| | 1 | F1 | F1 | 0 | F1 | F1 | F1 | 0 | 0 | F1 |
| XI | 3 | N2 | 0 | N4 | 0 | 0 | 0 | 0 | 0 | 0 |
| | 1 | 0 | 0 | 0 | 0 | 0 | 0 | 0 | 0 | 0 |
| XII | 3 | N3F3 | 0 | N4 | 0 | 0 | N1 | 0 | 0 | F1G1 |
| | 1 | F2 | 0 | 0 | 0 | 0 | 0 | 0 | 0 | F1 |
| XIII | 3 | F3 | F1 | F1 | F1 | 0 | 0 | 0 | N1F1 | 0 |
| | 1 | F2 | 0 | 0 | 0 | 0 | 0 | 0 | 0 | 0 |
| XIV | 3 | F1 | 0 | 0 | 0 | 0 | 0 | 0 | 0 | 0 |
| | 1 | 0 | 0 | 0 | 0 | 0 | 0 | 0 | 0 | 0 |
| XV | 3 | F1G1 | 0 | N1 | N1 | 0 | N1 | 0 | 0 | 0 |
| | 1 | 0 | 0 | F1 | 0 | 0 | 0 | 0 | 0 | 0 |
| XVI | 3 | N2F1 | N1 | N1 | F1 | 0 | N2 | N1 | 0 | N2 |
| | 1 | 0 | 0 | N1 | 0 | 0 | 0 | 0 | 0 | 0 |
| XVII | 3 | 0 | 0 | 0 | 0 | 0 | 0 | 0 | 0 | 0 |
| | 1 | 0 | 0 | 0 | 0 | 0 | 0 | 0 | 0 | 0 |
| XVIII | 3 | F1G1 | 0 | 0 | 0 | 0 | 0 | 0 | 0 | 0 |

TABLE 3-continued

POST-EMERGENT EFFECTS ON 24 SPECIES

| Species | Appl'n. Rate (lb/A) | | | | | | | | |
|---|---|---|---|---|---|---|---|---|---|
| XIX | 1 | 0 | 0 | 0 | 0 | 0 | 0 | 0 | 0 | 0 |
|  | 3 | F2 | F1 | N2F1 | F1 | 0 | N1 | 0 | 0 | F1 |
| XX | 1 | F1 | 0 | F1 | F1 | 0 | 0 | 0 | 0 | 0 |
|  | 3 | 0 | 0 | 0 | 0 | 0 | 0 | 0 | 0 | 0 |
| XXI | 1 | 0 | 0 | 0 | 0 | 0 | 0 | 0 | 0 | 0 |
|  | 3 | F1 | 0 | 0 | 0 | 0 | 0 | 0 | 0 | 0 |
| XXII | 1 | 0 | 0 | 0 | 0 | 0 | 0 | 0 | 0 | 0 |
|  | 3 | F1 | 0 | 0 | 0 | 0 | 0 | 0 | 0 | 0 |
| XXIII | 1 | 0 | 0 | 0 | 0 | 0 | 0 | 0 | 0 | 0 |
|  | 3 | 0 | 0 | 0 | 0 | 0 | 0 | 0 | 0 | 0 |
| XXIV | 1 | 0 | 0 | 0 | 0 | 0 | 0 | 0 | 0 | 0 |
|  | 3 | 0 | 0 | 0 | 0 | 0 | 0 | 0 | 0 | 0 |
| XXV | 1 | 0 | 0 | 0 | 0 | 0 | 0 | 0 | 0 | 0 |
|  | 3 | 0 | 0 | 0 | 0 | 0 | 0 | 0 | 0 | 0 |
|  | 1 | 0 | 0 | 0 | 0 | 0 | 0 | 0 | 0 | 0 |

| Species | Appl'n. Rate (lb/A) | Compound Nos. | | | | | | | | |
|---|---|---|---|---|---|---|---|---|---|---|
|  |  | 4824 | 4825 | 4826 | 4833 | 4834 | 4835 | 4837 | 4838 | 4839 |
| I | 3 | F1 | 0 | N1G1 | F3G3 | F2G1 | F2G2 | 0 | F2G2 | 0 |
|  | 1 | 0 | 0 | 0 | F3G3 | 0 | G1 | 0 | 0 | 0 |
| II | 3 | F1 | 0 | G1 | F3G3 | F2G1 | F2G2 | 0 | F2G1 | F1 |
|  | 1 | 0 | 0 | 0 | F3G3 | 0 | 0 | 0 | 0 | 0 |
| III | 3 | 0 | 0 | 0 | G1F1 | 0 | 0 | 0 | 0 | 0 |
|  | 1 | 0 | 0 | 0 | 0 | 0 | 0 | 0 | 0 | 0 |
| IV | 3 | 0 | 0 | 0 | F1 | 0 | 0 | 0 | 0 | 0 |
|  | 1 | 0 | 0 | 0 | 0 | 0 | 0 | 0 | 0 | 0 |
| V | 3 | 0 | 0 | 0 | F2G1 | 0 | 0 | 0 | 0 | 0 |
|  | 1 | 0 | 0 | 0 | F1 | 0 | 0 | 0 | 0 | 0 |
| VI | 3 | 0 | 0 | 0 | 0 | 0 | 0 | 0 | 0 | 0 |
|  | 1 | 0 | 0 | 0 | 0 | 0 | 0 | 0 | 0 | 0 |
| VII | 3 | 0 | 0 | 0 | F1 | 0 | 0 | 0 | 0 | 0 |
|  | 1 | 0 | 0 | 0 | 0 | 0 | 0 | 0 | 0 | 0 |
| VIII | 3 | F1N1 | ) | N1G1 | F3N3 | F3G1 | F2N1 | 0 | N1 | N1 |
|  | 1 | 0 | 0 | 0 | F3N2 | F1 | F1 | 0 | 0 | 0 |
| IX | 3 | 0 | 0 | F1G1 | F3G3 | F3G1 | F2 | 0 | F1 | 0 |
|  | 1 | 0 | 0 | 0 | F3G1 | F1 | F2 | 0 | F1 | 0 |
| X | 3 | F2G1 | F1 | 0 | F3G2 | F2G1 | F2G1 | F1 | F2 | 0 |
|  | 1 | F1 | 0 | 0 | F2G1 | F1 | F1 | 0 | F1 | 0 |
| XI | 3 | 0 | 0 | 0 | F3G2 | F1 | F1G1 | 0 | F1 | 0 |
|  | 1 | 0 | 0 | 0 | F1 | 0 | 0 | 0 | 0 | 0 |
| XII | 3 | F1 | 0 | 0 | F3G3 | F2G1 | F1G1 | 0 | F1 | 0 |
|  | 1 | 0 | 0 | 0 | F3G1 | 0 | F1 | 0 | 0 | 0 |
| XIII | 3 | 0 | 0 | N1 | F3 | F1 | F3 | F1 | F2 | N1 |
|  | 1 | 0 | 0 | 0 | F3 | 0 | F1 | 0 | F1 | 0 |
| XIV | 3 | 0 | 0 | 0 | F1 | 0 | F1 | 0 | 0 | 0 |
|  | 1 | 0 | 0 | 0 | F1 | 0 | 0 | 0 | 0 | 0 |
| XV | 3 | 0 | 0 | N1 | F2G2 | F1 | F1G1 | 0 | 0 | 0 |
|  | 1 | 0 | 0 | 0 | F2G1 | 0 | 0 | 0 | 0 | 0 |
| XVI | 3 | F2N1 | N1 | N1 | F3G3 | F2G1 | F2G1 | 0 | F2 | N1 |
|  | 1 | 0 | 0 | 0 | F3G3 | 0 | F1 | 0 | F1 | N1 |
| XVII | 3 | 0 | 0 | 0 | F2G1 | 0 | 0 | 0 | 0 | 0 |
|  | 1 | 0 | 0 | 0 | F1 | 0 | 0 | 0 | 0 | 0 |
| XVIII | 3 | 0 | 0 | 0 | F2G2 | 0 | 0 | 0 | 0 | 0 |
|  | 1 | 0 | 0 | 0 | F1 | 0 | 0 | 0 | 0 | 0 |
| XIX | 3 | N1F2 | N1F1 | N1 | F3G1 | F1 | F3 | F1 | F2G2 | 0 |
|  | 1 | F1 | N1 | 0 | F3 | 0 | F2 | 0 | F1 | 0 |
| XX | 3 | 0 | 0 | 0 | F1 | 0 | 0 | 0 | 0 | 0 |
|  | 1 | 0 | 0 | 0 | 0 | 0 | 0 | 0 | 0 | 0 |
| XXI | 3 | 0 | 0 | 0 | F2G2 | F1 | F2G1 | 0 | F1 | 0 |
|  | 1 | 0 | 0 | 0 | F2G1 | 0 | 0 | 0 | 0 | 0 |
| XXII | 3 | 0 | 0 | 0 | F2G1 | F1 | F2G1 | 0 | F1 | 0 |
|  | 1 | 0 | 0 | 0 | F2G1 | 0 | 0 | 0 | 0 | 0 |
| XXIII | 3 | 0 | 0 | 0 | F1G1 | 0 | 0 | 0 | 0 | 0 |
|  | 1 | 0 | 0 | 0 | F1 | 0 | 0 | 0 | 0 | 0 |
| XXIV | 3 | 0 | 0 | 0 | F1 | 0 | 0 | 0 | 0 | 0 |
|  | 1 | 0 | 0 | 0 | 0 | 0 | 0 | 0 | 0 | 0 |
| XXV | 3 | 0 | 0 | 0 | F1G1 | 0 | 0 | 0 | 0 | 0 |
|  | 1 | 0 | 0 | 0 | 0 | 0 | 0 | 0 | 0 | 0 |

| Species | Appl'n. Rate (lb/A) | Compound Nos. | | | | | | | | |
|---|---|---|---|---|---|---|---|---|---|---|
|  |  | 4840 | 4857 | 4858 | 4859 | 4860 | 4861 | 4862 | 4863 | 4864 |
| I | 3 | N1 | F1G1 | 0 | F1 | 0 | F1 | F1G1 | F3G3 | G1 |
|  | 1 | 0 | 0 | 0 | 0 | 0 | 0 | 0 | F2G2 | 0 |
| II | 3 | N1 | F2G1 | G1 | F1 | 0 | 0 | F1G1 | F3G3 | 0 |
|  | 1 | 0 | 0 | 0 | 0 | 0 | 0 | 0 | F2G2 | 0 |
| III | 3 | 0 | 0 | 0 | 0 | 0 | 0 | 0 | F2G2 | 0 |
|  | 1 | 0 | 0 | 0 | 0 | 0 | 0 | 0 | F1 | 0 |
| IV | 3 | 0 | 0 | 0 | 0 | 0 | 0 | 0 | F1G1 | 0 |

TABLE 3-continued
POST-EMERGENT EFFECTS ON 24 SPECIES

| Species | Appl'n Rate (lb/A) | | | | | | | | | |
|---|---|---|---|---|---|---|---|---|---|---|
| V | 3 | 0 | 0 | 0 | 0 | 0 | 0 | 0 | 0 | 0 |
|  | 1 | 0 | 0 | 0 | 0 | 0 | 0 | 0 | F3G2 | 0 |
| VI | 3 | 0 | 0 | 0 | 0 | 0 | 0 | 0 | F1 | 0 |
|  | 1 | 0 | 0 | 0 | 0 | 0 | 0 | 0 | 0 | 0 |
| VII | 3 | 0 | 0 | 0 | 0 | 0 | 0 | 0 | 0 | 0 |
|  | 1 | 0 | 0 | 0 | 0 | 0 | 0 | 0 | F1 | 0 |
| VIII | 3 | N1 | F1 | N1 | N1 | 0 | 0 | N1F1 | F3N3 | 0 |
|  | 1 | 0 | 0 | 0 | 0 | 0 | 0 | F1 | F2 | 0 |
| IX | 3 | N1 | F1 | 0 | 0 | 0 | 0 | 0 | F3G2 | N1F1 |
|  | 1 | 0 | 0 | 0 | 0 | 0 | 0 | 0 | F2 | 0 |
| X | 3 | 0 | F1 | F2G1 | F1 | F1 | F1 | F2 | F3G2 | F1 |
|  | 1 | 0 | F1 | F2 | 0 | 0 | F1 | F1 | F2 | F1 |
| XI | 3 | 0 | 0 | 0 | 0 | 0 | 0 | 0 | F2G1 | 0 |
|  | 1 | 0 | 0 | 0 | 0 | 0 | 0 | 0 | F2G1 | 0 |
| XII | 3 | 0 | 0 | 0 | 0 | 0 | F1 | 0 | F2G1 | 0 |
|  | 1 | 0 | 0 | 0 | 0 | 0 | 0 | 0 | F1 | 0 |
| XIII | 3 | 0 | F2 | N1F1 | N1F1 | 0 | N1 | F1 | F3G1 | 0 |
|  | 1 | 0 | F1 | N1 | 0 | 0 | 0 | 0 | F2 | 0 |
| XIV | 3 | 0 | 0 | 0 | 0 | 0 | 0 | 0 | F1 | 0 |
|  | 1 | 0 | 0 | 0 | 0 | 0 | 0 | 0 | 0 | 0 |
| XV | 3 | 0 | 0 | 0 | 0 | 0 | 0 | 0 | F2G1 | 0 |
|  | 1 | 0 | 0 | 0 | 0 | 0 | 0 | 0 | F1 | 0 |
| XVI | 3 | N1 | F2N1 | F1N1 | 0 | 0 | 0 | F1 | F3G3 | F1 |
|  | 1 | 0 | F1N1 | 0 | 0 | 0 | 0 | 0 | F1 | F1 |
| XVII | 3 | 0 | 0 | 0 | 0 | 0 | 0 | 0 | F2G2 | 0 |
|  | 1 | 0 | 0 | 0 | 0 | 0 | 0 | 0 | F1 | 0 |
| XVIII | 3 | 0 | 0 | 0 | 0 | 0 | 0 | 0 | F3G2 | 0 |
|  | 1 | 0 | 0 | 0 | 0 | 0 | 0 | 0 | 0 | 0 |
| XIX | 3 | 0 | F2G1 | F1 | 0 | F1 | 0 | F1 | F3G3 | F1 |
|  | 1 | 0 | F1 | 0 | 0 | 0 | 0 | 0 | F2 | F1 |
| XX | 3 | 0 | 0 | 0 | 0 | 0 | 0 | 0 | F1 | 0 |
|  | 1 | 0 | 0 | 0 | 0 | 0 | 0 | 0 | 0 | 0 |
| XXI | 3 | 0 | 0 | 0 | 0 | 0 | 0 | 0 | F3G2 | 0 |
|  | 1 | 0 | 0 | 0 | 0 | 0 | 0 | 0 | F2G1 | 0 |
| XXII | 3 | 0 | 0 | 0 | 0 | 0 | 0 | 0 | F3G2 | 0 |
|  | 1 | 0 | 0 | 0 | 0 | 0 | 0 | 0 | F2G1 | 0 |
| XXIII | 3 | 0 | 0 | 0 | 0 | 0 | 0 | 0 | F2G2 | 0 |
|  | 1 | 0 | 0 | 0 | 0 | 0 | 0 | 0 | F2G2 | 0 |
| XXIV | 3 | 0 | 0 | 0 | 0 | 0 | 0 | 0 | F2G1 | 0 |
|  | 1 | 0 | 0 | 0 | 0 | 0 | 0 | 0 | F2G1 | 0 |
| XXV | 3 | 0 | 0 | 0 | 0 | 0 | 0 | 0 | F2G1 | 0 |
|  | 1 | 0 | 0 | 0 | 0 | 0 | 0 | 0 | F1G1 | 0 |

| Species | Appl'n Rate (lb/A) | Compound Nos. | | | | | | | | |
|---|---|---|---|---|---|---|---|---|---|---|
|  |  | 4865 | 4866 | 4869 | 4870 | 4871 | 4872 | 4873 | 4874 | 4875 |
| I | 3 | F2G1 | F1G1 | 0 | 0 | G1 | F3G3 | 0 | F2G2 | 0 |
|  | 1 | 0 | 0 | 0 | 0 | 0 | F2G1 | 0 | 0 | 0 |
| II | 3 | F2G1 | F1G1 | 0 | F1G1 | 0 | F3G3 | F1 | F3G3 | F1G1 |
|  | 1 | F1 | 0 | 0 | 0 | 0 | F3G2 | 0 | F1 | 0 |
| III | 3 | 0 | 0 | 0 | 0 | 0 | F2G2 | 0 | 0 | 0 |
|  | 1 | 0 | 0 | 0 | 0 | 0 | F1G1 | 0 | 0 | 0 |
| IV | 3 | 0 | 0 | 0 | 0 | 0 | F1G1 | 0 | 0 | 0 |
|  | 1 | 0 | 0 | 0 | 0 | 0 | 0 | 0 | 0 | 0 |
| V | 3 | 0 | 0 | 0 | 0 | 0 | F2G2 | 0 | 0 | 0 |
|  | 1 | 0 | 0 | 0 | 0 | 0 | F2 | 0 | 0 | 0 |
| VI | 3 | 0 | 0 | 0 | 0 | 0 | 0 | 0 | 0 | 0 |
|  | 1 | 0 | 0 | 0 | 0 | 0 | 0 | 0 | 0 | 0 |
| VII | 3 | 0 | 0 | 0 | 0 | 0 | F1 | 0 | 0 | 0 |
|  | 1 | 0 | 0 | 0 | 0 | 0 | 0 | 0 | 0 | 0 |
| VIII | 3 | F2 | 0 | 0 | F2N1 | N1F1 | F3G1 | 0 | F2 | 0 |
|  | 1 | F1 | 0 | 0 | F1 | 0 | F3 | 0 | 0 | 0 |
| IX | 3 | F1 | 0 | 0 | F2 | F1 | F3 | F1 | F2 | F1 |
|  | 1 | F1 | 0 | 0 | F1 | 0 | F3 | 0 | F1 | 0 |
| X | 3 | F2G1 | F1 | F1 | F2G1 | F1 | F2G1 | F2G1 | F1 | F2 |
|  | 1 | F1 | 0 | F1 | F1 | F1 | F2 | F1 | F1 | F1 |
| XI | 3 | F2G2 | 0 | 0 | F2G2 | 0 | F1 | 0 | 0 | 0 |
|  | 1 | G1 | 0 | 0 | F1 | 0 | 0 | 0 | 0 | 0 |
| XII | 3 | F3G3 | 0 | 0 | F1G1 | 0 | F1 | 0 | 0 | 0 |
|  | 1 | F1 | 0 | 0 | F1 | 0 | 0 | 0 | 0 | 0 |
| XIII | 3 | F2 | 0 | 0 | F2 | 0 | F3G3 | F1 | F1 | 0 |
|  | 1 | F1 | 0 | 0 | F1 | 0 | F3 | 0 | 0 | 0 |
| XIV | 3 | 0 | 0 | 0 | 0 | 0 | F1 | 0 | 0 | 0 |
|  | 1 | 0 | 0 | 0 | 0 | 0 | F1 | 0 | 0 | 0 |
| XV | 3 | F1 | 0 | 0 | F1 | 0 | F2 | 0 | 0 | 0 |
|  | 1 | 0 | 0 | 0 | 0 | 0 | F1 | 0 | 0 | 0 |
| XVI | 3 | F3G2 | F1 | N1 | N1F1 | N1 | F3G2 | F1 | N1F1 | 0 |
|  | 1 | F1 | 0 | 0 | 0 | 0 | F1 | 0 | 0 | 0 |
| XVII | 3 | 0 | 0 | 0 | 0 | 0 | F2G2 | 0 | 0 | 0 |
|  | 1 | 0 | 0 | 0 | 0 | 0 | F2 | 0 | 0 | 0 |

TABLE 3-continued

POST-EMERGENT EFFECTS ON 24 SPECIES

| Species | Appl'n. Rate (lb/A) | | | | | | | | | |
|---------|---------------------|---|---|---|---|---|---|---|---|---|
| XVIII | 3 | 0 | 0 | 0 | 0 | 0 | F2G2 | 0 | 0 | 0 |
|  | 1 | 0 | 0 | 0 | 0 | 0 | F2 | 0 | 0 | 0 |
| XIX | 3 | F3G3 | F1 | F1 | F2 | F1 | F3G1 | F1 | F2 | 0 |
|  | 1 | F2 | 0 | 0 | F1 | 0 | F2 | F1 | F1 | 0 |
| XX | 3 | 0 | 0 | 0 | 0 | 0 | F1 | 0 | 0 | 0 |
|  | 1 | 0 | 0 | 0 | 0 | 0 | 0 | 0 | 0 | 0 |
| XXI | 3 | F2 | 0 | 0 | 0 | 0 | F3G1 | 0 | 0 | 0 |
|  | 1 | F1 | 0 | 0 | 0 | 0 | F2 | 0 | 0 | 0 |
| XXII | 3 | F2 | 0 | 0 | 0 | 0 | F3G1 | 0 | 0 | 0 |
|  | 1 | F1 | 0 | 0 | 0 | 0 | F2 | 0 | 0 | 0 |
| XXIII | 3 | 0 | 0 | 0 | G1 | 0 | F2G1 | 0 | 0 | 0 |
|  | 1 | 0 | 0 | 0 | 0 | 0 | F1 | 0 | 0 | 0 |
| XXIV | 3 | 0 | 0 | 0 | 0 | 0 | F2 | 0 | 0 | 0 |
|  | 1 | 0 | 0 | 0 | 0 | 0 | F1 | 0 | 0 | 0 |
| XXV | 3 | 0 | 0 | 0 | 0 | 0 | F2G1 | 0 | 0 | 0 |
|  | 1 | 0 | 0 | 0 | 0 | 0 | F2 | 0 | 0 | 0 |

| Species | Appl'n. Rate (lb/A) | Compound Nos. | | | | | | | | |
|---------|---------------------|------|------|------|------|------|------|------|------|------|
|  |  | 4876 | 4877 | 4878 | 4879 | 4881 | 4882 | 4883 | 4884 | 4885 |
| I | 3 | 0 | 0 | F3G2 | F1 | F3G3 | F1 | 0 | F1 | F1G1 |
|  | 1 | 0 | 0 | F1 | 0 | F3G2 | 0 | 0 | 0 | 0 |
| II | 3 | 0 | F1 | F3G2 | F1 | F3G3 | F1 | F1 | F1G1 | F2G2 |
|  | 1 | 0 | 0 | F2 | F1 | F3G3 | 0 | 0 | F1 | F1 |
| III | 3 | 0 | 0 | 0 | 0 | 0 | 0 | 0 | 0 | 0 |
|  | 1 | 0 | 0 | 0 | 0 | 0 | 0 | 0 | 0 | 0 |
| IV | 3 | 0 | 0 | 0 | 0 | 0 | 0 | 0 | 0 | 0 |
|  | 1 | 0 | 0 | 0 | 0 | 0 | 0 | 0 | 0 | 0 |
| V | 3 | 0 | 0 | 0 | 0 | 0 | 0 | 0 | 0 | 0 |
|  | 1 | 0 | 0 | 0 | 0 | 0 | 0 | 0 | 0 | 0 |
| VI | 3 | 0 | 0 | 0 | 0 | 0 | 0 | 0 | 0 | 0 |
|  | 1 | 0 | 0 | 0 | 0 | 0 | 0 | 0 | 0 | 0 |
| VII | 3 | 0 | 0 | 0 | 0 | F1 | 0 | 0 | 0 | 0 |
|  | 1 | 0 | 0 | 0 | 0 | 0 | 0 | 0 | 0 | 0 |
| VIII | 3 | 0 | 0 | F1 | F3 | F3 | 0 | 0 | 0 | N1 |
|  | 1 | 0 | 0 | 0 | F2 | F3 | 0 | 0 | 0 | 0 |
| IX | 3 | 0 | F1 | F2 | F2 | F2 | F1 | F1 | 0 | F1 |
|  | 1 | 0 | 0 | F1 | F1 | F2 | 0 | 0 | — | — |
| X | 3 | F2 | F1 | F3G2 | F2G1 | F2 | F2 | F2 | F2 | F2G2 |
|  | 1 | 0 | F1 | F2G1 | F1 | F1 | F1 | 0 | F1 | F2 |
| XI | 3 | 0 | F1 | F3G3 | F2G1 | F3G2 | 0 | 0 | 0 | F1 |
|  | 1 | 0 | 0 | F2G2 | 0 | F2 | 0 | 0 | 0 | 0 |
| XII | 3 | 0 | F1 | F3G3 | F1 | F3G1 | F1 | 0 | 0 | F1 |
|  | 1 | 0 | 0 | F2G1 | F1 | F2 | 0 | 0 | 0 | 0 |
| XIII | 3 | 0 | F1 | F2 | F1 | F1 | 0 | 0 | F1 | 0 |
|  | 1 | 0 | 0 | F1 | F1 | F1 | 0 | 0 | 0 | 0 |
| XIV | 3 | 0 | 0 | 0 | 0 | 0 | 0 | 0 | 0 | N1 |
|  | 1 | 0 | 0 | 0 | 0 | 0 | 0 | 0 | 0 | 0 |
| XV | 3 | 0 | 0 | F1 | 0 | 0 | 0 | 0 | 0 | N1 |
|  | 1 | 0 | 0 | 0 | 0 | 0 | 0 | 0 | 0 | 0 |
| XVI | 3 | 0 | F1 | F3N2 | F1 | F1N1 | N1F1 | 0 | N1 | N1 |
|  | 1 | 0 | 0 | F2N1 | 0 | F1 | 0 | 0 | 0 | N1 |
| XVII | 3 | 0 | 0 | 0 | 0 | 0 | 0 | 0 | 0 | 0 |
|  | 1 | 0 | 0 | 0 | 0 | 0 | 0 | 0 | 0 | 0 |
| XVIII | 3 | 0 | 0 | 0 | 0 | 0 | 0 | 0 | 0 | 0 |
|  | 1 | 0 | 0 | 0 | 0 | 0 | 0 | 0 | 0 | 0 |
| XIX | 3 | F1 | F1 | F3 | F2 | F3G1 | F1 | F1 | F1 | F1 |
|  | 1 | 0 | F1 | F3 | F1 | F3 | F1 | 0 | 0 | F1 |
| XX | 3 | 0 | 0 | 0 | 0 | 0 | 0 | 0 | 0 | 0 |
|  | 1 | 0 | 0 | 0 | 0 | 0 | 0 | 0 | 0 | 0 |
| XXI | 3 | 0 | 0 | 0 | 0 | 0 | 0 | 0 | 0 | 0 |
|  | 1 | 0 | 0 | 0 | 0 | 0 | 0 | 0 | 0 | 0 |
| XXII | 3 | 0 | 0 | 0 | 0 | 0 | 0 | 0 | 0 | 0 |
|  | 1 | 0 | 0 | 0 | 0 | 0 | 0 | 0 | 0 | 0 |
| XXIII | 3 | 0 | 0 | 0 | 0 | 0 | 0 | 0 | 0 | 0 |
|  | 1 | 0 | 0 | 0 | 0 | 0 | 0 | 0 | 0 | 0 |
| XXIV | 3 | 0 | 0 | 0 | 0 | 0 | 0 | 0 | 0 | 0 |
|  | 1 | 0 | 0 | 0 | 0 | 0 | 0 | 0 | 0 | 0 |
| XXV | 3 | 0 | 0 | 0 | 0 | 0 | 0 | 0 | 0 | 0 |
|  | 1 | 0 | 0 | 0 | 0 | 0 | 0 | 0 | 0 | 0 |

The use of many of the growth regulator compounds may be demonstrated by treatment of soybeans (*soja max*) to increase the number of seed pods and by treating tomato plants (*Lycopersicum esculentum*) to increase fruit set. In an illustrative experiment, *Soja max* (Evans variety) and *Lycopersicum esculentum* (Tiny Tim variety) were grown in 4-inch pots (one plant per pot) filled with greenhouse potting soil (2 parts good top soil, 1½ parts builders' sand, 1½ parts peat, fertilized with 5 lb. of 12-12-6 fertilizer and 5 lb. of finely ground limestone per cu. yd.). Aqueous spray formulations were prepared and the potted plants were sprayed at a spray volume of 40 gal. per acre and at application rates of 16, 4, 1 and ¼ oz. per acre. The spray mixtures were prepared by dissolving the proper amount of growth regulator compound in 15 ml. of acetone, adding 2 ml. of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 80 ml by addition of a 0.156 wt. percent aqueous solution of liquid non-ionic dispersant (90 wt. percent active trimethylnonyl polyethylene glycol ether, Tergitol TMN-10). Two replicates were sprayed at all application rates. For comparative purposes, plants were also sprayed at 40 gal./acre with water. The number of seed pods and of fruit as percentage of arithmetic mean of the numbers on untreated plants was observed within approximately three weeks after spray treatment and the results are tabulated below. The severity of growth regulatory effect on the plants was estimated on a scale of 0 to 10 and is also recorded in the following table:

cordance with established practice in the art. An aqueous spray is usually prepared by mixing a wettable powder or emulsifiable concentrate formulation of a growth regulator with a relatively large amount of water for form a dispersion.

Wettable powders comprise intimate, finely divided mixtures of growth regulator compounds, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensa-

TABLE 4

GROWTH REGULATING EFFECTS ON TWO SPECIES

| | | Lycopersicum esculentum | | Soja max | |
|---|---|---|---|---|---|
| Comp'd. No. | Rate oz/A | Severity of Growth Regulating Effect | Fruit Count Percent in Comparison to Untreated Plants | Severity of Growth Regulating Effect | Pod Count Percent in Comparison to Untreated Plants |
| 4061 | 16 | 5.5 | 700 | 5 | 133 |
| | 4 | 2.5 | 900 | 3.5 | 126 |
| | 1 | 1 | 900 | 3 | 136 |
| 4436 | 16 | 0.5 | 191 | 3 | 100 |
| | 4 | 0 | 163 | 0 | 118 |
| | 1 | 0 | 109 | 0 | 91 |
| 4337 | 16 | 0.5 | 191 | 1 | 123 |
| | 4 | 0 | 136 | 0 | 141 |
| | 1 | 0 | 177 | 0 | 105 |
| 4338 | 16 | 3 | 204 | 3.5 | 145 |
| | 4 | 0.5 | 232 | 1 | 118 |
| | 1 | 0 | 272 | 0 | 105 |
| 4345 | 16 | 0 | 150 | 0 | 86 |
| | 4 | 0 | 163 | 0 | 105 |
| | 1 | 0 | 95 | 0 | 100 |
| 4346 | 16 | 0 | 106 | 0 | 95 |
| | 4 | 0 | 95 | 0 | 105 |
| | 1 | 0 | 95 | 0 | 86 |
| 4347 | 16 | 3 | 117 | 1 | 109 |
| | 4 | 1 | 163 | 0 | 91 |
| | 1 | 0 | 109 | 0 | 105 |
| 4348 | 16 | 0.5 | 150 | 0 | 114 |
| | 4 | 0 | 109 | 0 | 118 |
| | 1 | 0 | 109 | 0 | 100 |
| 4350 | 16 | 7 | 232 | 2 | 123 |
| | 4 | 2 | 177 | 0.5 | 100 |
| | 1 | 1 | 163 | 0 | 86 |
| 4354 | 16 | 1.5 | 128 | 2 | 160 |
| | 4 | 0 | 42 | 1 | 145 |
| | 1 | 0 | 64 | 0 | 106 |
| 4533 | 16 | 6.5 | 136 | 3 | 137 |
| | 4 | 4.5 | 136 | 1 | 120 |
| | 1 | 3 | 232 | 0.5 | 120 |

The information presented in tabular form herein will enable a worker in the art to make a selection from among the growth regulator compounds of the invention and to make some judgment with regard to application rates, depending upon the effect which is desired. It may be seen, for example, that total kills of some species of vegetation may occur at application rates as high as 5 to 10 lb. per acre, whereas beneficial effects may be observed on living plants at application rates of 1 lb. per acre or less.

The growth regulator compounds are usually applied in combination with inert carriers or diluents, as in aqueous sprays, granules and dust formulations in action of ethylene oxide with alkylphenols.

Emulsifiable concentrates of the growth regulator compounds comprise in each instance, a solution of growth regulator compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

In general, the growth regulators are applied in formulations which desirably contain from 0.1 percent to 95 percent of a compound of formula (1) and from 0.1 to 75 percent of a carrier or surfactant. However, direct application to plant seeds prior to planting may be accomplished in some instances by mixing powdered solid growth regulator with seed to obtain a substantially uniform coating which is very thin and comprises only one or two percent by weight or less, based on the weight of the seed. In most instances, however, a non-phytotoxic solvent, such as methanol is employed as a carrier to facilitate the uniform distribution of growth regulator on the surface of the seed.

When a compound is to be applied to the soil, as for a pre-emergence application, granular formulations are sometimes more convenient than sprays. A typical granular formation comprises the growth regulator compound dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation.

We claim:

1. A compound of the formula:

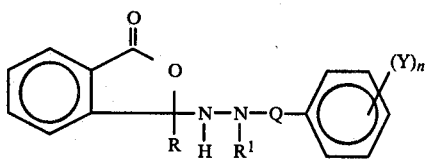

in which Q represents one of the following structures:

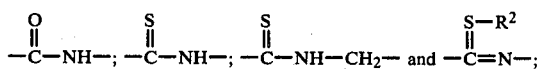

R is methyl or ethyl, $R^1$ is H or lower alkyl, $R^2$ is lower alkyl and Y represents substituents, alike or unlike, selected from the group consisting of lower alkyl, lower alkoxy, lower alkylthio, bromo, chloro, fluoro, cyano and trifluoromethyl and n=0 to 3, or a hydrohalide salt thereof.

2. The method of regulating the growth of plants comprising applying to the plants, the seed or the soil an effective amount of a compound as specified in claim 1.

3. The method of regulating the growth of plants which comprises applying to the plants pre- or post-emergently an effective amount of a composition comprising from 0.1 percent to 95 percent of a compound of claim 1 in combination with from 0.1 to 75 weight percent of a carrier or surfactant.

4. The method of increasing fruit set of crop plants which comprises applying to the plant foliage an effective amount of a compound of claim 1 in combination with an inert carrier and a surfactant.

5. The method of claim 4 in which the crop plants are of the species *Lycopersicum esculentum*.

6. The method of claim 4 in which the crop plants are of the species *Soja max*.

7. The compound according to claim 1 in which R and $R^1$ are methyl, Q is —CSNH— and $(Y)_n$ is 4-fluoro.

8. The compound according to claim 1 in which R and $R^1$ are methyl, Q is —CSNH— and $(Y)_n$ is 3-methyl.

9. The compound according to claim 1 in which R and $R^1$ are methyl, Q is —CSNH— and $(Y)_n$ is 4-bromo.

10. The compound according to claim 1 in which R and $R^1$ are methyl, Q is —CSNH— and n is zero.

11. The compound according to claim 1 in which R and $R^1$ are methyl, Q is —CSNH— and $(Y)_n$ is 2-fluoro.

12. The compound according to claim 1 in which R and $R^1$ are methyl, Q is —CSNH— and $(Y)_n$ is 4-methyl.

13. The compound according to claim 1 in which R and $R^1$ are methyl, Q is —CSNH— $(Y)_n$ is 3-trifluoromethyl.

14. The compound according to claim 1 in which R and $R^1$ are methyl, Q is —CSNH— and $(Y)_n$ is 3,4-dichloro.

15. The compound according to claim 1 in which R and $R^1$ are methyl, Q is —CONH— and n is zero.

16. The compound according to claim 1 in which R and $R^1$ are methyl, Q is —CSNH— and $(Y)_n$ is 4-iodo.

17. The compound according to claim 1 in which R and $R^1$ are methyl, Q is —CSNH— and $(Y)_n$ is 4-cyano.

18. The compound according to claim 1 in which R and $R^1$ are methyl, Q is —CSNH— and $(Y)_n$ is 2,5-dimethyl.

19. The compound according to claim 1 in which R and $R^1$ are methyl, Q is —CSNH— and $(Y)_n$ is 3-chloro.

20. The compound according to claim 1 in which R is methyl, $R^1$ is hydrogen, Q is —CONH— and n is zero.

21. The compound according to claim 1 in which R and $R^1$ are methyl, Q is —CONH— and $(Y)_n$ is 2-fluoro.

22. The compound according to claim 1 in which R and $R^1$ are methyl, Q is —CONH— and $(Y)_n$ is 3-fluoro.

23. The compound according to claim 1 in which R and $R^1$ are methyl, Q is —CONH— and $(Y)_n$ is 4-ethyl.

24. The compound according to claim 1 in which R and $R^1$ are methyl, Q is —CSNH— and $(Y)_n$ is 3,5-dichloro.

25. The compound according to claim 1 in which R and $R^1$ are methyl, Q is —CSNH— and $(Y)_n$ is 4-butyl.

26. The compound according to claim 1 in which R and $R^1$ are methyl, Q is —CSNH— and $(Y)_n$ is 3-bromo.

27. The compound according to claim 1 in which R and $R^1$ are methyl, Q is —CSNH— and $(Y)_n$ is 2-methoxy.

28. The compound according to claim 1 in which R and $R^1$ are methyl, Q is —CSNH— and $(Y)_n$ is 3-chloro-4-methyl.

29. The compound according to claim 1 in which R and $R^1$ are methyl, Q is —CSNH— and $(Y)_n$ is 2-trifluoromethyl.

30. The compound according to claim 1 in which R and $R^1$ are methyl, Q is —CSNH— and $(Y)_n$ is 2,6-dichloro.

31. The compound according to claim 1 in which R and $R^1$ are methyl, Q is —CSNH— and $(Y)_n$ is 4-methoxy.

32. The compound according to claim 1 in which Q is

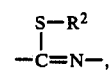

R, $R^1$ and $R^2$ are methyl, $(Y)_n$ is 3-fluoro and the compound is a hydriodide salt.

33. The compound according to claim 1 in which Q is

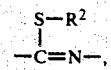

R, R¹ and R² are methyl, (Y)$_n$ is 4-ethyl and the compound is a hydriodide salt.

34. The compound according to claim 1 in which Q is

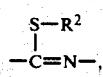

R and R¹ are methyl, R² is ethyl, n is zero and the compound is a hydriodide salt.

35. The compound according to claim 1 in which Q is

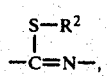

R, R¹ and R² are methyl, (Y)$_n$ is 4-chloro and the compound is a hydriodide salt.

36. The compound according to claim 1 in which R is methyl, R¹ is hydrogen, Q is —CSNH— and (Y)$_n$ is 3-chloro-4-methyl.

37. The compound according to claim 1 in which R is methyl, R¹ is hydrogen, Q is —CSNH— and (Y)$_n$ is 2,4-dimethyl.

38. The compound according to claim 1 in which R and R¹ are methyl, Q is —CSNH— and (Y)$_n$ is 2-methyl.

39. The compound according to claim 1 in which R and R¹ are methyl, Q is —CSNH— and (Y)$_n$ is 3-methoxy.

40. The compound according to claim 1 in which R and R¹ are methyl, Q is —CSNH— and (Y)$_n$ is 4-chloro.

41. The compound according to claim 1 in which R and R¹ are methyl, Q is —CONH— and (Y)$_n$ is 3-methylthio.

42. The compound according to claim 1 in which R and R¹ are methyl, Q is —CONH— and (Y)$_n$ is 3-methoxy.

43. The compound according to claim 1 in which R and R¹ are methyl, Q is —CONH— and (Y)$_n$ is 2-methoxy.

44. The compound according to claim 1 in which R and R¹ are methyl, Q is —CONH— and (Y)$_n$ is 4-methyl.

45. The compound according to claim 1 in which R and R¹ are methyl, Q is —CONH— and (Y)$_n$ is 2-ethoxy.

46. The compound according to claim 1 in which R and R¹ are methyl, Q is —CONH— and (Y)$_n$ is 2,6-dichloro.

47. The compound according to claim 1 in which R and R¹ are methyl, Q is —CONH— and (Y)$_n$ is 4-chloro-3-trifluoromethyl.

48. The compound according to claim 1 in which R and R¹ are methyl, Q is —CONH— and (Y)$_n$ is 2-methyl-5-chloro.

49. The compound according to claim 1 in which R and R¹ are methyl, Q is —CONH— and (Y)$_n$ is 3-chloro-4,6-dimethoxy.

50. The compound according to claim 1 in which R and R¹ are methyl, Q is —CONH— and (Y)$_n$ is 2-chloro-6-metyl.

51. The compound according to claim 1 in which R and R¹ are methyl, Q is —CONH— and (Y)$_n$ is 4-butoxy.

52. The compound according to claim 1 in which R and R¹ are methyl, Q is —CONH— and (Y)$_n$ is 2,6-dimethyl-4-bromo.

53. The compound according to claim 1 in which R is ethyl, R¹ is methyl, Q is —CONH— and (Y)$_n$ is 4-methyl.

54. The method of regulating the growth of plants comprising applying to the plants, the seed or the soil an effective amount of a compound as specified in claims 7, 8, 9, 10, 11, 12, 13, 14, 15, 16, 17, 18, 19, 20, 22, 24, 26, 32, 33, 34, 39, 40, 42, 47 or 49.

* * * * *